US009446330B2

(12) United States Patent
Benevides et al.

(10) Patent No.: US 9,446,330 B2
(45) Date of Patent: *Sep. 20, 2016

(54) HPLC CAPILLARY COLUMN DEVICE

(71) Applicant: Waters Technologies Corporation, Milford, MA (US)

(72) Inventors: Christopher C. Benevides, Tiverton, MA (US); Robert Collamati, Taunton, MA (US); Bruce J. Compton, Lexington, MA (US); Theodore Dourdeville, Marion, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/892,830

(22) Filed: May 13, 2013

(65) Prior Publication Data

US 2013/0248700 A1  Sep. 26, 2013

Related U.S. Application Data

(63) Continuation of application No. 11/576,385, filed as application No. PCT/US2004/033079 on Oct. 7, 2004, now Pat. No. 8,496,818.

(51) Int. Cl.
*B01D 15/22* (2006.01)
*G01N 30/60* (2006.01)
(Continued)

(52) U.S. Cl.
CPC ............ *B01D 15/22* (2013.01); *G01N 30/02* (2013.01); *G01N 30/6091* (2013.01); *G01N 30/7266* (2013.01); *G01N 30/30* (2013.01)

(58) Field of Classification Search
USPC ................................................. 436/178, 173
See application file for complete search history.

(56) References Cited

U.S. PATENT DOCUMENTS 4,209,696 A   6/1980  Fite
4,392,873 A *  7/1983  Brockington ............... 95/84
(Continued)

FOREIGN PATENT DOCUMENTS

JP   61005466      1/1986
JP   62145151      9/1987
JP   2004079305    3/2004

OTHER PUBLICATIONS

Nabshima et al., "Biological and Environmental Analysis by Using LS/3DQMS", Chromatography, 1997, 10.15, vol. 18, No. 4, pp. 254-255; 5 pages.

*Primary Examiner* — Katherine Zalasky
(74) *Attorney, Agent, or Firm* — Schmeiser, Olsen & Watts LLP

(57) ABSTRACT

A high pressure liquid chromatography (HPLC) capillary column device, system and method for processing a HPLC sample with a cartridge housing a packed capillary column; at least one inlet connection to the capillary column for a sample fluid; and at least one outlet connection from the capillary column for the sample fluid. The outlet connection is able to accommodate either a spray tip for atomizing the sample fluid or a transport tube for transporting the sample fluid from a spray tip column to a spray tip. Inlet connections enable supply of electrical power to the capillary column through electrical connections disposed within the cartridge housing; and gas for evaporating the sample liquid is supplied to at least one outlet connection from the capillary column for the sample fluid through a gas supply line within the cartridge housing. The temperature of the sample liquid can be controlled through a heat connection.

32 Claims, 7 Drawing Sheets

(51) Int. Cl.
*G01N 30/72* (2006.01)
*G01N 30/02* (2006.01)
*G01N 30/30* (2006.01)

(56) References Cited

U.S. PATENT DOCUMENTS

| | | |
|---|---|---|
| 4,958,529 A | 9/1990 | Vestal |
| 4,982,097 A | 1/1991 | Silvon et al. |
| 5,103,093 A | 4/1992 | Sakairi et al. |
| 5,240,616 A | 8/1993 | Kato et al. |
| 5,266,192 A | 11/1993 | Ligon et al. |
| 5,641,400 A * | 6/1997 | Kaltenbach et al. ...... 210/198.2 |
| 6,117,317 A * | 9/2000 | Dickson et al. ........... 210/198.2 |
| 6,459,080 B1 * | 10/2002 | Yin et al. ...................... 250/288 |
| 2002/0110902 A1 * | 8/2002 | Prosser et al. ............. 435/287.1 |
| 2002/0158195 A1 * | 10/2002 | Andersson et al. .......... 250/288 |
| 2004/0113068 A1 * | 6/2004 | Bousse et al. ................ 250/288 |
| 2004/0124085 A1 * | 7/2004 | Tai et al. ...................... 204/600 |
| 2005/0258360 A1 * | 11/2005 | Whitehouse et al. ........ 250/288 |

\* cited by examiner

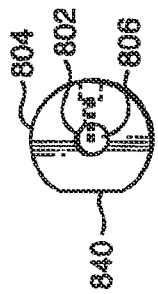
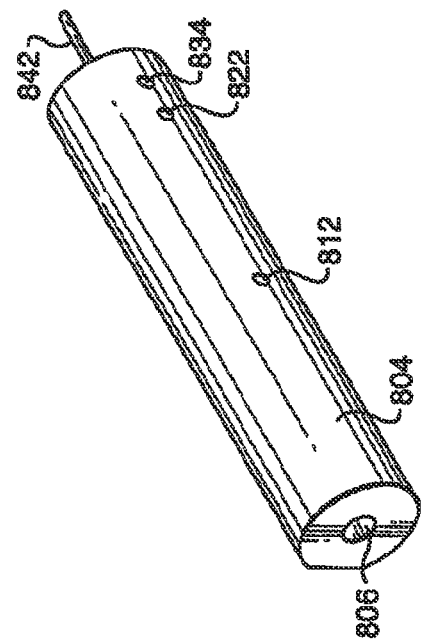
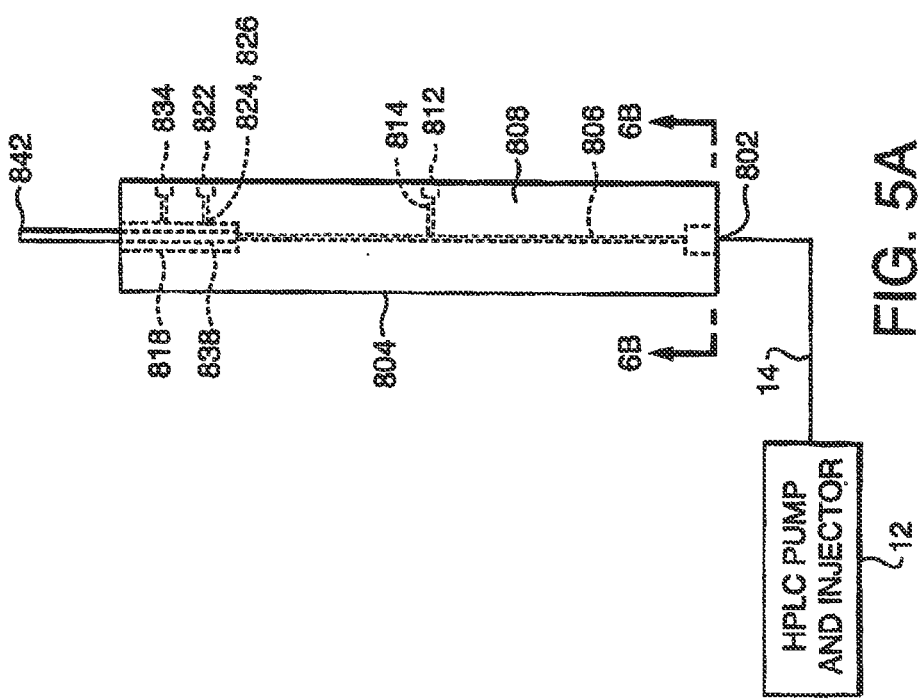
FIG. 5B
FIG. 5C
FIG. 5A

HPLC CAPILLARY COLUMN DEVICE

RELATED APPLICATIONS

This application is a continuation application claiming the benefit of the filing date of U.S. patent application, Ser. No. 11/576,385 filed Jan. 22, 2008, a 371 of international application number PCT/US2004/033079 filed on Oct. 7, 2004, the contents of each of which is incorporated by reference herein in its entirety.

BACKGROUND OF THE INVENTION

Capillary columns used for high pressure liquid chromatography (HPLC) are fragile and difficult to manipulate. A high level of care must be taken when handling and connecting the capillary to an HPLC system for analysis by a mass spectrometer. This is typically a tedious and time consuming process. Also, temperature control of the capillary column is generally difficult to establish.

SUMMARY OF THE INVENTION

It is an object of this invention to provide a HPLC system for interfacing between a chromatographic system and a mass spectrometer.

It is an object of this invention to provide a HPLC capillary column device of reduced size which also reduces the risk of damage and reduces handling time via a cassette cartridge arrangement.

It is an object of this invention to provide a HPLC capillary column device which enables accurate temperature control and heating capabilities.

The present invention is directed to a high pressure liquid chromatography (HPLC) capillary column device for processing a HPLC sample. The device has a cartridge housing, and the cartridge housing comprises: a packed capillary column inside the cartridge housing; at least one inlet connection to the capillary column for a sample fluid; and at least one outlet connection from the capillary column for the sample fluid. The outlet connection is able to accommodate one of a spray tip for atomizing the sample fluid and a transport tube for transporting the sample fluid from a spray tip column to a spray tip. An inlet connection enables supply of electrical power to the capillary column through electrical connections disposed within the cartridge housing; and an inlet connection enables supply of a gas to the at least one outlet connection from the capillary column for the sample fluid through a gas supply line disposed within the cartridge housing, with the gas supply line being fluidically coupled to the outlet connection.

The HPLC capillary column device can further comprise a heat connection enabling a heat supply to be coupled to the capillary column and the heat supply can control the temperature of the HPLC device during the HPLC processing. The heat supply can be either electrical or a heated fluid. Voltage applied to the sample liquid by the electrical power supply ionizes at least a portion of the sample liquid.

The invention can also be in the form of a cartridge for a high pressure liquid chromatography (HPLC) capillary column device for processing a HPLC sample, with the device comprising a cartridge housing as described above.

The housing can have a multi-sided cross-section and the capillary column can be disposed in a straight line from the inlet connection to the outlet connection, or alternatively, in a curvilinear line from the inlet connection to the outlet connection.

The housing can have a substantially curvilinear cross-section which can further comprise at least one portion that is not uniformly disposed with respect to the substantially curvilinear cross-section. The portion that is not uniformly disposed is capable of acting as an alignment key for the cartridge to be inserted into a mass spectrometer interface.

The present invention can be in the form of a high pressure liquid chromatography (HPLC) system for interfacing between a chromatographic system and a mass spectrometer. The HPLC system comprises: a HPLC capillary column cartridge cassette, the cartridge cassette including connections for controlling gas flow, temperature and voltage applied to a liquid sample within the capillary column. The cartridge cassette is capable of receiving a sample and chromatographic data from the chromatographic system. The system further comprises a mass spectrometer interface device, with the mass spectrometer interface device including a cartridge cassette holder for holding the HPLC capillary cartridge cassette. The cartridge cassette holder is capable of transmitting the liquid sample in a charged atomized condition to the mass spectrometer. In addition, the gas flow, temperature and voltage of the cartridge cassette are capable of being controlled by the mass spectrometer.

The present invention also provides a method of processing a sample from a HPLC capillary column device with the HPLC capillary column device comprising a cartridge for a packed capillary column. The method is performed by: choosing an appropriate cartridge for one of a procedure being conducted and a compound being detected; inserting the cartridge into a mass spectrometer interface; connecting a connection on the cartridge with a gas supply line supplied to the sample liquid through the gas supply line for evaporating at least a portion of the sample liquid; evaporating at least a portion of the sample liquid; connecting a connection on the cartridge with an electrical power supply line for atomizing the sample liquid at a liquid junction of the packed capillary column; atomizing the sample liquid at a liquid junction of the packed capillary column; and establishing flow from a chromatographic system and to a mass spectrometer through the mass spectrometer interface by injecting a sample liquid into the chromatographic system;

Furthermore, the method can also comprise the steps of maintaining temperature of the capillary column in a range of 5 to 70.degree. C. above ambient temperature; and analyzing, by the mass spectrometer, flow emerging as a spray from a stage of the mass spectrometer interface. A spray tip can be employed for the spray to the mass spectrometer. A transport tube can be employed for transporting the spray to the mass spectrometer, with the transport tube being either rigid or flexible.

BRIEF DESCRIPTION OF THE DRAWINGS

FIG. 5A is a plan view of an HPLC capillary column device according to an alternate arrangement of the third embodiment of the present invention having a transport tube to a spray tip.

FIG. 5B is an end view of the HPLC capillary column device according to the alternate arrangement of the third embodiment of the present invention according to FIG. 5A having a transport tube to a spray tip.

FIG. 5C is a perspective view of the HPLC capillary column device according to the alternate arrangement of the third embodiment of the present invention of FIGS. 5A and 5B.

DETAILED DESCRIPTION OF EXEMPLARY EMBODIMENTS

The present invention provides an HPLC capillary column device which facilitates the interface of the device with a mass spectrometer. To facilitate the description of the present invention, the features of the prior art are described as follows.

Figure 1:
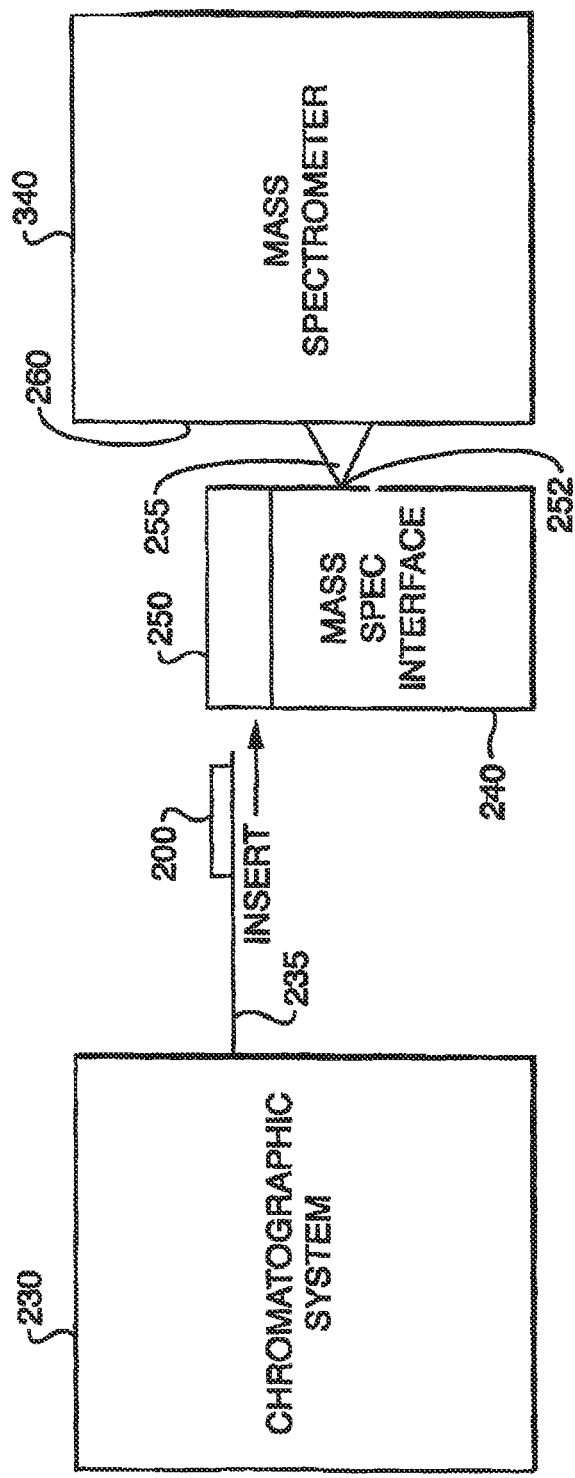
FIG. 1 is a schematic view of the HPLC system of the present invention.

FIG. 1 is a schematic view of the HPLC system of the present invention. HPLC capillary column cassette 200 is provided to facilitate the interface of the electrospray mass spectrometry unit. In particular, a spray tip, voltage source and connections 24 and 26, and the desolvation gas flow are now readily interfaced with a mass spectrometer 340 having a front side 260. The chromatographic system 230 provides the chromatographic spectra for a sample (not shown). The chromatographic spectra are output through a connection 235 to the HPLC column cassette 200. The HPLC column cassette is then inserted into a cassette holder 250 of mass spectrometer interface device 240. The mass spectrometer interface device 240 interfaces by means of a spray 255 of the sample which emerges from stage 252 which travels to the front side 260 of mass spectrometer 340. Typically, the mass spectrometer 340 controls the parameters such as the temperature, desolvation gas flow and the applied voltage for the HPLC column cassette 200 but control can also be exerted from the mass spectrometer interface device 240 or from the chromatographic system 230. Also, although the mass spectrometer interface device 240 is illustrated in FIG. 1 as being separate from the chromatographic system 230 and from the mass spectrometer 340, the interface device 240 can also be integral with either the chromatographic system 230 or the mass spectrometer 340. In addition, the HPLC column cassette 200 can be designed into several different specific embodiments as follows.

First Embodiment

Figure 2A:
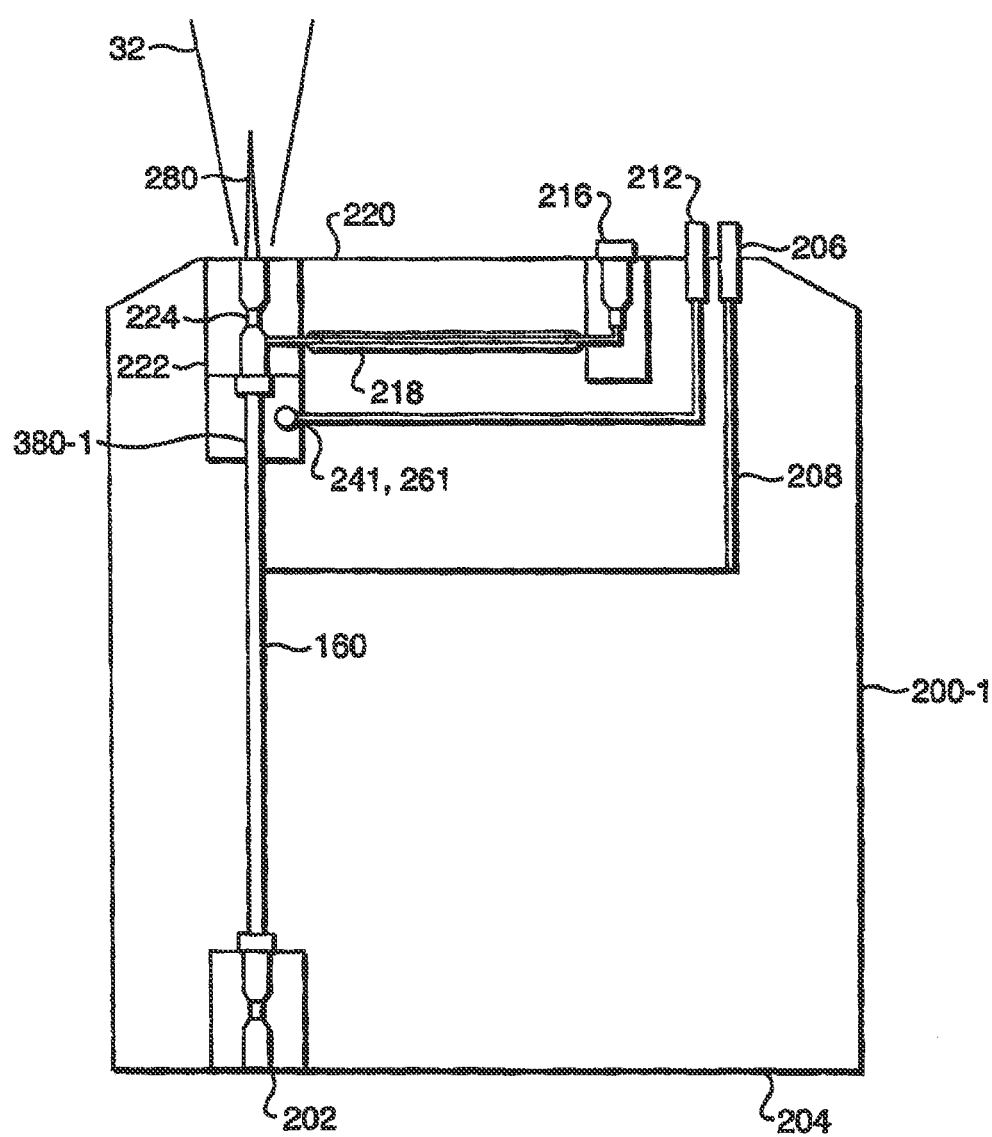
FIG. 2A is a plan view of an HPLC capillary column device according to a first embodiment of the present invention having a spray tip.

FIG. 2A is a plan view of an HPLC capillary column device according to the first embodiment of the present invention. The HPLC pump and injector injects a liquid sample through an inlet connection 202 contained within the rear side surface 204 of a cassette cartridge 200-1. The capillary column 160 is disposed within the cassette cartridge 200. The capillary column is packed in a manner commonly applied by those skilled in the art. A heat source connection 206, a voltage source connection 212, and a gas source connection 216 are each contained within the front side surface 220 of the cassette cartridge 200-1.

Heat provided through the column heat source connection 206, sufficient to maintain the temperature of the HPLC device in a range typically of 5 to 70.degree. C. above ambient temperature, is conducted through a flow tube or channel 208 disposed internally within the cassette cartridge 200-1. The heat source connection 206 is fluidically coupled, when the heat source is a heated fluid, or electrically coupled, when the heat source is an electrical resistance wire, to the flow tube or channel 208 that surrounds the capillary column 160 within the cassette cartridge 200-1 to provide a means for accurate temperature control and heating of the sample fluid within the capillary column 160.

The voltage provided through the voltage source connection 212, typically in the range of 4 KV DC, is directed by the voltage connections 241 and 261 to atomize and disperse the liquid sample emerging from the outlet 224 of the capillary column 160 that is within the conductive adapter 222 into a very fine spray of electrically charged droplets. The spray tip 280 immediately downstream of the capillary column outlet 224 within the conductive adapter 222 directs the sample spray 32 towards the mass spectrometer 340.

The gas, typically but not limited to nitrogen, provided through the gas source connection 216 again provides desolvation gas flow at pressures and temperatures sufficient to increase the rate of evaporation of the solvent of the liquid sample during the electrospray ionization (ESI) process occurring as a result of the voltage applied through the voltage connections 241 and 261. The gas source connection 216 is fluidically coupled to gas flow tube or channel 218 internally disposed within the cassette cartridge 200-1, the gas flow tube or channel 218 in turn being fluidically coupled to the spray tip 280 through the conductive collar 222.

Figure 2B:
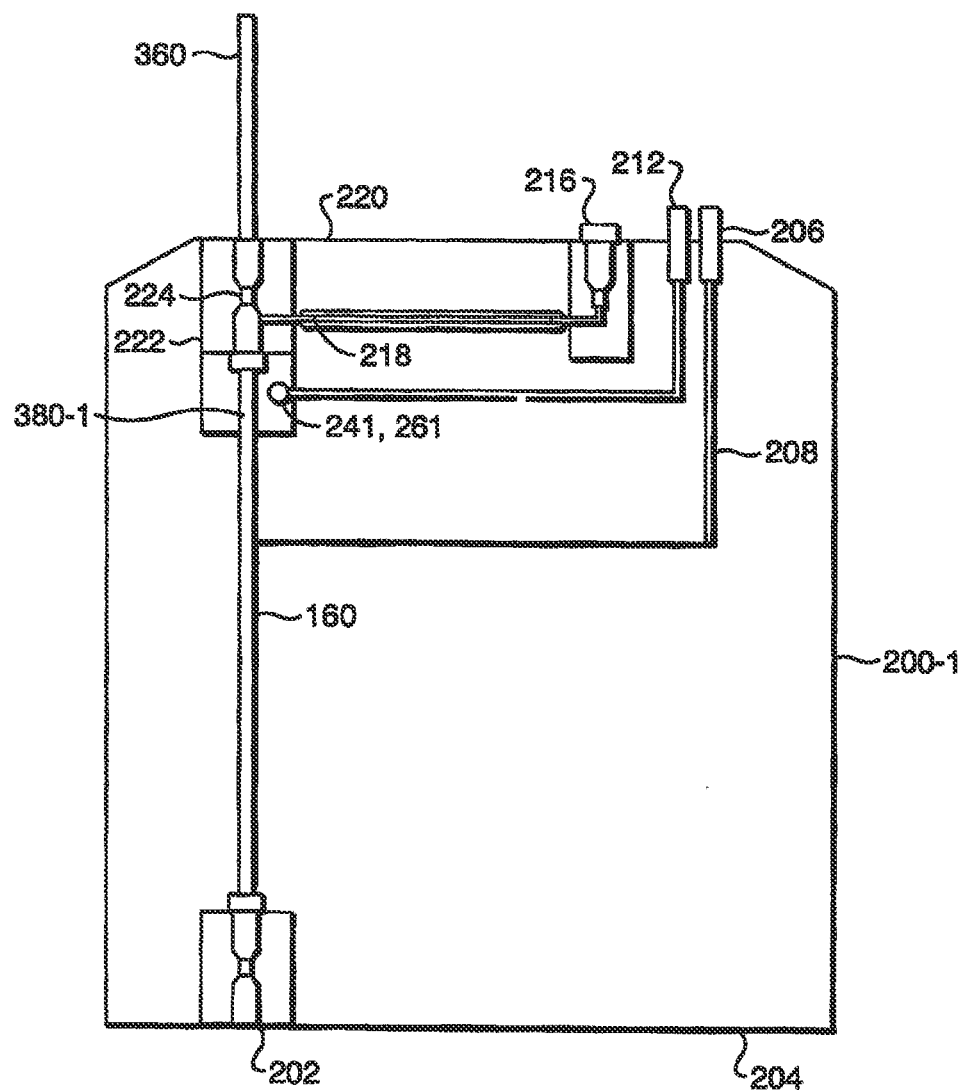
FIG. 2B is a plan view of an HPLC capillary column device according to an alternate arrangement of the first embodiment of the present invention having a transport tube to a spray tip.

FIG. 2B is an alternate arrangement of the first embodiment disclosed in FIG. 2A. The only difference is that instead of spray tip 280 being immediately downstream of capillary column 160, the transport tube 360 is immediately downstream of capillary column 160. In all other respects, the cassette cartridge 200 is identical to that disclosed in FIGS. 1A and 1B. The application of the voltage for atomization at the voltage connections 241 and 261 occurs at the liquid junction 380-1. The gas evaporates the liquid sample solvent within the conductive adapter 222.

Second Embodiment

Figure 3:
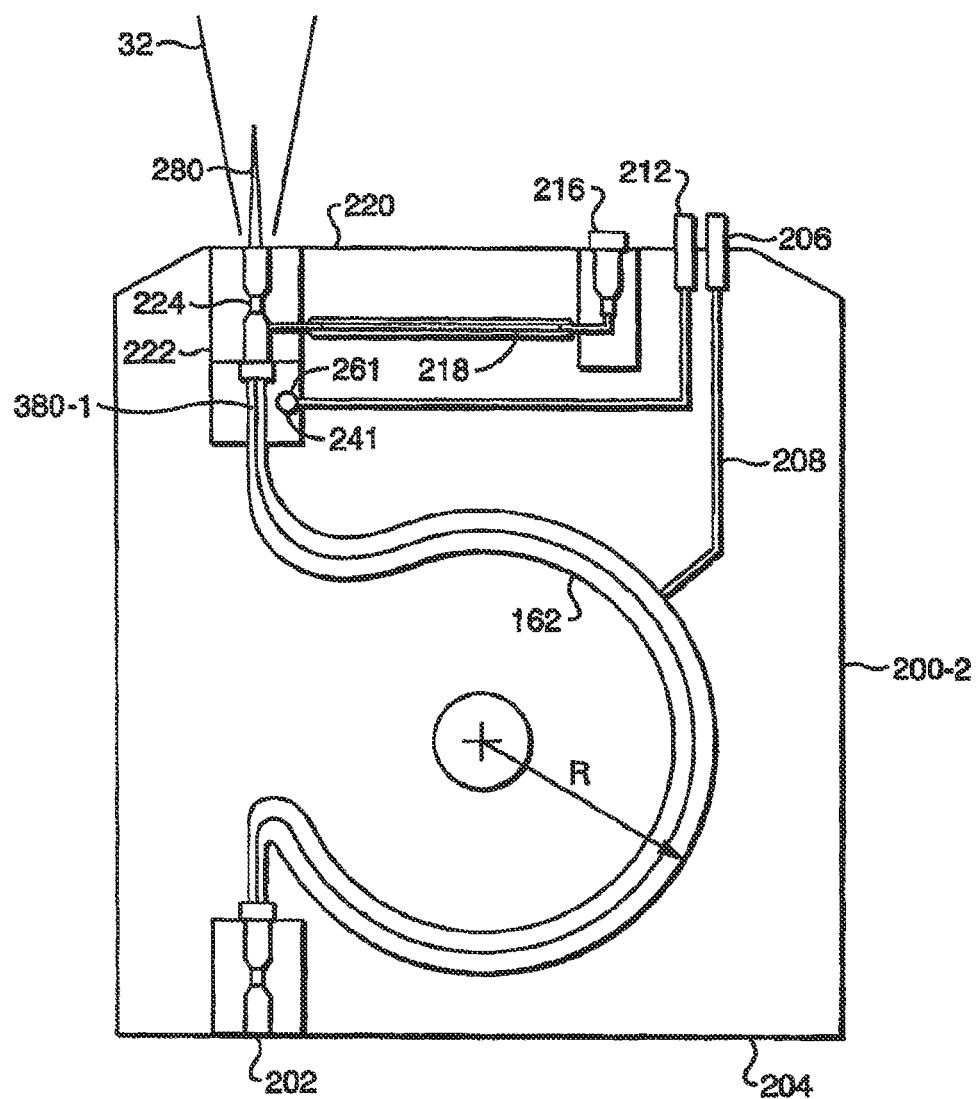
FIG. 3 is a plan view of an HPLC capillary column device according to a second embodiment of the present invention having a spray tip.

FIG. 3 is a plan view of a second embodiment of the present invention where cassette cartridge 200-2 contains the same components as illustrated in FIG. 2A for cassette cartridge 200-1, including the spray tip 280, but instead of a straight capillary column, such as capillary column 160 in FIGS. 2A and 2B, a coiled capillary column 162 is provided instead within what is typically a circular enclosure 270 of radius R. In all other respects, the coiled capillary column cassette cartridge 200-2 is the same as cassette cartridge 200-1. Furthermore, those skilled in the art recognize that while the coiled capillary column cassette cartridge 200-2 is shown with a spray tip configuration as in FIG. 2A, the transport tube configuration described in FIG. 2B can be applied to the coiled column cartridge 200-2 as well.

Third Embodiment

Figure 4B:
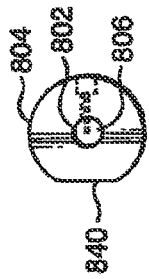
FIG. 4B is an end view of the HPLC capillary column device according to the third embodiment of the present invention according to FIG. 4A having a spray tip.
Figure 4C:
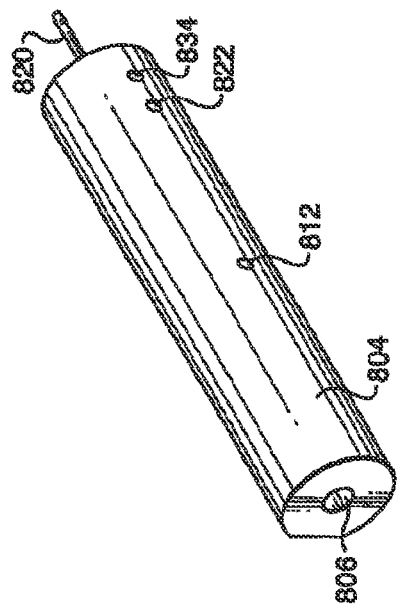
FIG. 4C is a perspective view of the HPLC capillary column device according to the third embodiment of the present invention of FIGS. 4A and 4B.
Figure 4A:
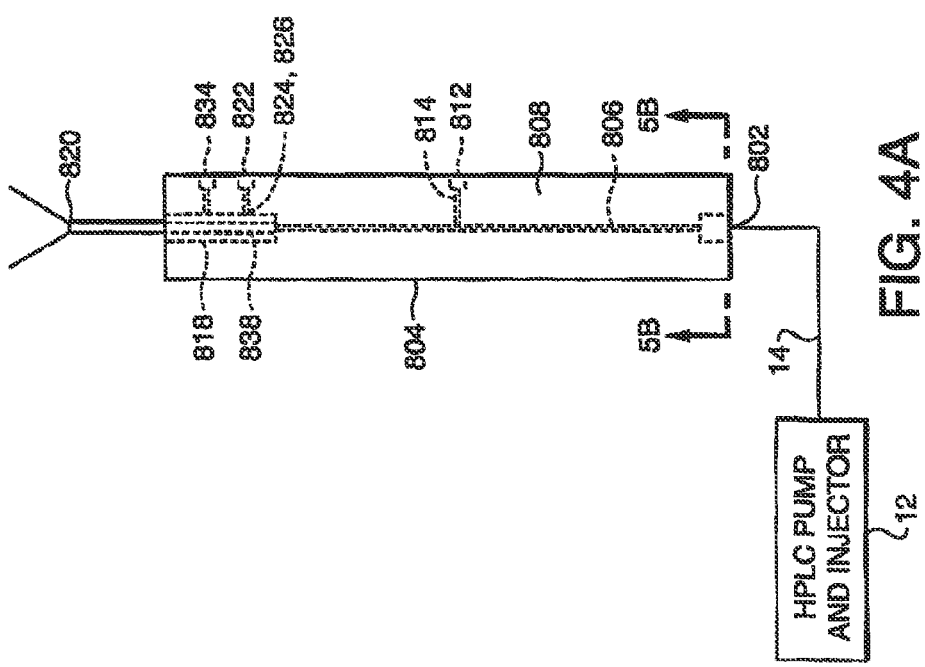
FIG. 4A is a plan view of an HPLC capillary column device according to a third embodiment of the present invention having a spray tip.

FIG. 4A is a plan view of the third embodiment of the present invention. The third embodiment differs from the first and second embodiments in that a tubular cartridge rather than a flat cartridge houses the capillary column. Specifically, the HPLC pump and injector 12 injects the liquid sample into inlet connection 802 of tubular cassette cartridge 804. The tubular cassette cartridge 804 encloses the capillary column 806 typically along the centerline of the tubular cartridge 804, which typically is comprised of, but is not limited to, a circular cross-section. A column heat block 808 in the tubular cassette cartridge 804 provides insulation of heat flow to the capillary column 806 that is provided through heat source connection 812. The heat source connection 812 is formed on the outer surface of the tubular cassette cartridge 804 and, depending on whether the heat source is a heated fluid or an electrical resistance source, fluidically or electrically couples tube or channel 814 to the capillary column 806.

Further downstream, at the outlet end of the tubular cassette cartridge 804, a conductive adapter 818 surrounds a spray tip 828. A voltage source connection 822 penetrates the conductive adapter 818 by way of voltage connections 824 and 826. The voltage provided through the voltage source connection 822, again typically in the range of 4 KV DC, is directed by the voltage connections 824 and 826 to atomize and disperse the liquid sample 14 emerging from the end of the capillary column 806 at the liquid junction interface 838 that is within the conductive adapter 818 into a very fine spray of electrically charged droplets. The spray tip 820 immediately downstream of the end of the capillary column 806 within the conductive collar 818 directs the sample spray 32 towards the mass spectrometer 240, which in this case interfaces with the tubular cassette cartridge 804 by way of an interfacing port 844 contained within a cassette holder 850 that is contained within the mass spectrometer 240. In this case, the cassette holder 850 is designed to facilitate the interconnection with the now tubular-shaped cartridge 804, as discussed below for FIGS. 4B and 4C.

As before with respect to the first and second embodiments, the gas, typically but not limited to nitrogen, provided through the gas source connection 834 again provides desolvation gas flow at pressures and temperatures sufficient to increase the rate of solvent evaporation during the electrospray ionization (ESI) process. The gas source connection 834 is fluidically coupled to gas flow tube or channel 836 internally disposed within the tubular cassette cartridge 804 and which in turn is fluidically coupled to the spray tip 820 through the conductive adapter 818.

FIG. 4B is an elevation view of the inlet end of the tubular cassette cartridge 804 of FIG. 5A. The alignment key 840 is provided to facilitate proper insertion of the tubular cartridge 804 into the cassette holder 850 within the mass spectrometer interface 240.

FIG. 4C is a perspective view of the tubular cassette cartridge 804 of FIG. 4A showing the inlet connection 806, the heat source connection 812, the voltage source connection 822, the gas source connection 834, and the spray tip 820.

FIG. 5A is a plan view of an alternate arrangement of the third embodiment of the present invention illustrated in FIG. 4A. The only difference is that instead of spray tip 820 being immediately downstream of capillary column 806, the transport tube 842 is immediately downstream of capillary column 806. As is the case for the transport tube 360 of FIG. 2B, the transport tube enables transport of the atomized charged droplets to a mass spectrometer that is a distance away from the chromatographic system 230. In all other respects, the tubular cassette cartridge 804 is identical to that disclosed in FIG. 7A. As a result, FIG. 5B is identical to FIG. 4B. The only difference between FIG. 5C and FIG. 4C is the presence of the transport tube 842 instead of the spray tip 820.

Fourth Embodiment

Figure 6B:
FIG. 6B is an end view of the HPLC capillary column device according to the alternate arrangement of the third embodiment of the present invention according to FIG. 6A having a transport tube to a spray tip.
Figure 6C:
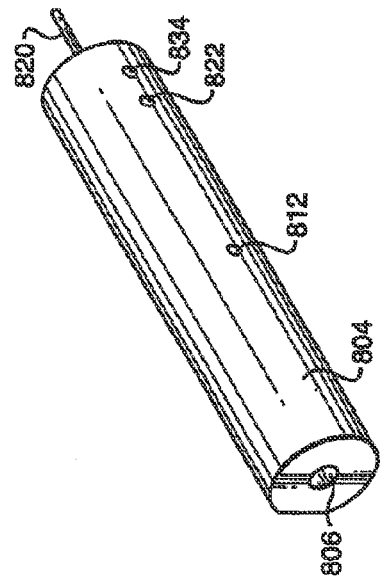
FIG. 6C is a perspective view of the HPLC capillary column device according to the alternate arrangement of the third embodiment of the present invention of FIGS. 6A and 6B.
Figure 6A:
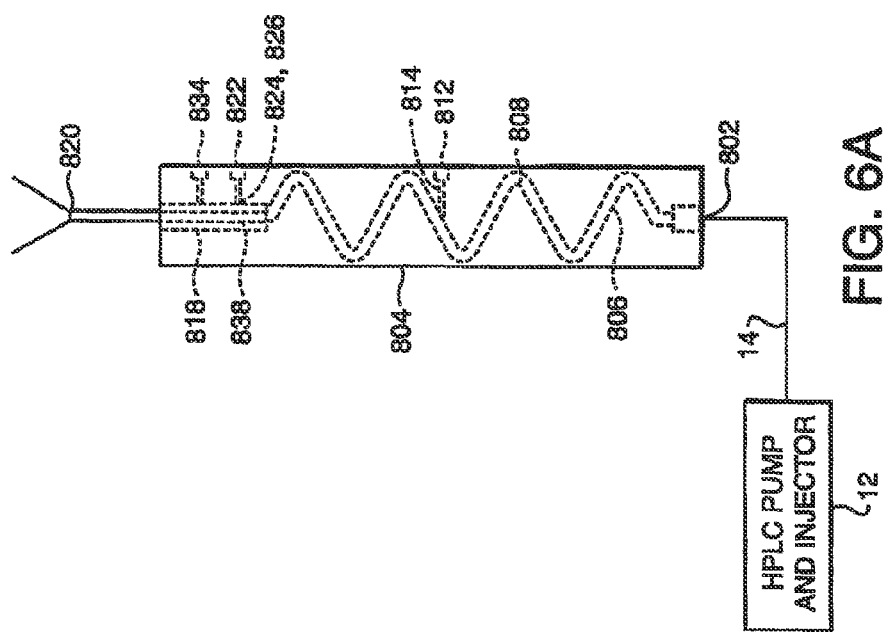
FIG. 6A is a plan view of a fourth embodiment of the present invention of FIG. 4 or 5A.

FIG. 6A is a plan view of a fourth embodiment of the present invention of FIG. 4A or 5A. In this case, the tubular cassette cartridge 804 of FIG. 4A or of FIG. 5A incorporates, instead of a straight capillary column 806, a coiled or helical capillary column 856 within the column heat block 808 Either a spray tip 820 or a transport tube to a spray tip 842 can be employed as is obvious to those skilled in the art. In all other respects, the tubular cassette cartridge 804, as shown in FIGS. 6A through 6C can be constructed and used in a similar manner as shown in FIGS. 4A-4C and FIGS. 5A-5C.

With respect to the method of using the first, second, third and fourth embodiments, referring to FIG. 1, the user chooses an appropriate cartridge, shown generically as cartridge cassette 200 to represent cartridge cassettes 200-1, 200-2 or 804 of FIGS. 2A through 6C as appropriate, for the procedure being conducted or the compound being detected. The user inserts either cartridge 200-1, 200-2 or 804 into the mass spectrometer interface 240 and makes the connections to the respective gas line 216 or 834, the electrical power for the voltage connection 212 or 822 and from the temperature control mechanism as represented by column heat connections 206 or 812. The user establishes flow from the chromatographic system 230 and to the mass spectrometer 340 through the mass spectrometer interface 240. The sample is injected into the chromatographic system 230 and emerges from the stage 252 as a spray 255 to be analyzed by the mass spectrometer 340 to obtain the desired results. When using a cartridge with a transport tube, such as transport tube 360 in FIG. 3B, or transport tube 842 in FIGS. 5A and 5C or the cartridge 200-2 in FIG. 3 when equipped with a transport tube, the transport tube can be either rigid or flexible. The design of the stage 252 can be such that either a rigid or flexible transport tube can be accommodated, as is obvious to those skilled in the art.

The invention has now been explained with reference to specific embodiments. Other embodiments will be apparent to those of ordinary skill in the art in view of the foregoing description. It is not intended that this invention be limited except as indicated by the appended claims and their full scope equivalents.

What is claimed is:

1. A liquid chromatography column device for processing a sample, the device having a cartridge housing, the cartridge housing comprising:

a separation column inside the cartridge housing;

at least two inlet connections in communication with the separation column, the at least two inlet connections comprising a first inlet connection that includes an electrical connection and a second inlet connection that receives a sample fluid;

at least one column outlet connection in communication with the separation column; and a liquid junction at a portion of a downstream end of the separation column, the liquid junction adjacent to an outlet of the at least one column outlet connection, wherein the electrical connection of the first inlet connection is constructed and arranged to apply a voltage to the sample fluid at the liquid junction at the portion of the downstream end of the separation column for atomizing at least a portion of sample fluid at the liquid junction prior to output from the at least one column outlet connection.

2. The device of claim 1, wherein the separation column includes a packed column.

3. The device of claim 1, further comprising a plurality of electrical connections positioned inside the cartridge housing, and wherein the electrical connection of the first inlet connection provides electrical power to the separation column through the electrical connections positioned inside the cartridge housing.

4. The device of claim 1, further comprising a third inlet connection that receives a gas.

5. The device of claim 4, wherein the third inlet connection supplies the gas to the at least one column outlet connection through a gas supply line disposed within the cartridge housing, wherein the third inlet connection is downstream of the liquid junction and between the liquid junction and the outlet of the at least one column outlet connection.

6. The device of claim 5, wherein the gas includes a heated desolvation gas for evaporating the sample fluid, the gas supply line fluidically coupled to the at least one column outlet connection.

7. The device of claim 5, wherein the gas is supplied to the sample fluid through the gas supply line and evaporates at least a portion of the sample fluid.

8. The device of claim 1, further comprising a heat connection that couples a heat supply to the separation column.

9. The device of claim 8, wherein the heat supply controls a temperature of the device.

10. The device of claim 8, wherein the heat supply is one of (a) electrical and (b) a heated fluid.

11. The device of claim 1, wherein the separation column is disposed in a straight line from at least one inlet connection of the at least two inlet connections to the at least one column outlet connection.

12. The device of claim 1, wherein the separation column is disposed in a curvilinear line from at least one inlet connection of the at least two inlet connections to the at least one column outlet connection.

13. The device of claim 1, wherein the housing has a substantially curvilinear cross-section.

14. The device of claim 13, wherein the substantially curvilinear cross-section further comprises at least one portion that is not uniformly disposed with respect to the substantially curvilinear cross-section, and wherein the at least one portion that is not uniformly disposed is capable of acting as an alignment key for the device to be inserted into a mass spectrometer interface.

15. The device of claim 1, wherein the at least one column outlet connection is constructed and arranged to accommodate immediately downstream of the separation column one of a spray tip for atomizing the sample fluid and a transport tube for transporting the sample fluid from the separation column to a spray tip, and wherein the voltage is applied by the first inlet connection to the sample fluid prior to the transport tube transporting the sample fluid from the separation column to the spray tip.

16. The device of claim 4, further comprising a conductive adapter about the liquid junction coupled to the electrical connection, wherein a liquid sample solvent is evaporated by the gas of the third inlet connection at the conductive adapter, wherein the conductive adapter is between the liquid junction and the outlet of the at least one column outlet connection.

17. The device of claim 1, wherein the cartridge housing has a first side and a second side opposite the first side, wherein the second inlet connection is at the first side of the cartridge housing and the first inlet connection is at the second side of the cartridge housing.

18. The device of claim 1, wherein the portion of sample fluid is atomized and ionized in the cartridge housing.

19. A liquid chromatography system for interfacing between a chromatographic system and a mass spectrometer, the system comprising:
   a column cartridge cassette, the cartridge cassette comprising:
      a separation column;
      at least two inlet connections, the at least two inlet connections comprising a first inlet connection including an electrical connection that provides a voltage and a second inlet connection inlet that receives a sample fluid; and
      at least one column outlet connection in communication with the separation column; and
   a liquid junction at a portion of a downstream end of the separation column, the liquid junction adjacent to an outlet of the at least one column outlet connection, wherein the electrical connection of the first inlet connection is constructed and arranged to apply a voltage to the sample fluid at the liquid junction for atomizing at least a portion of sample fluid at the liquid junction prior to output from the at least one column outlet connection.

20. The system of claim 19, wherein the separation column is a packed column.

21. The system of claim 19, further comprising a third inlet connection that receives a gas.

22. The system of claim 21, wherein the third inlet connection supplies the gas to the at least one column outlet connection through a gas supply line disposed within the cartridge housing, wherein the third inlet connection is downstream of the liquid junction and between the liquid junction and the outlet of the at least one column outlet connection.

23. The system of claim 22, wherein the gas includes a heated desolvation gas for evaporating the sample fluid, the gas supply line fluidically coupled to the at least one column outlet connection.

24. The system of claim 23, wherein the gas is supplied to the sample fluid through the gas supply line and evaporates at least a portion of the sample fluid.

25. The system of claim 19, further comprising a heat connection that couples a heat supply to the separation column.

26. The system of claim 19, wherein a voltage applied to the sample fluid by the first inlet connection ionizes at least a portion of the sample fluid.

27. The system of claim 19, wherein the at least one outlet connection is constructed and arranged to accommodate immediately downstream of the separation column one of a spray tip for atomizing the sample fluid and a transport tube for transporting the sample fluid from a spray tip the separation column to a spray tip, and wherein the voltage is applied by the first inlet connection to the sample fluid prior to the transport tube transporting the sample fluid from the separation column to the spray tip.

28. The system of claim 19, wherein the mass spectrometer controls at least one of a gas flow, a temperature and a voltage at the cartridge cassette.

29. The system of claim 19, further comprising:
a mass spectrometer interface device, the mass spectrometer interface device including a cartridge cassette holder for holding the column cartridge cassette, the cartridge cassette holder constructed and arranged to transmit the sample in a charged atomized condition to the mass spectrometer.

30. The system of claim 19, wherein the mass spectrometer interface device is integral with one of the mass spectrometer and the chromatographic system.

31. The system of claim 19, wherein the cartridge housing has a first side and a second side opposite the first side, wherein the second inlet connection is at the first side of the cartridge housing and the first inlet connection is at the second side of the cartridge housing.

32. The system of claim 19, wherein the portion of sample fluid is atomized and ionized in the cartridge housing.

\* \* \* \* \*

UNITED STATES PATENT AND TRADEMARK OFFICE
CERTIFICATE OF CORRECTION

| | | |
|---|---|---|
| PATENT NO. | : 9,446,330 B2 | Page 1 of 1 |
| APPLICATION NO. | : 13/892830 | |
| DATED | : September 20, 2016 | |
| INVENTOR(S) | : Christopher C. Benevides et al. | |

It is certified that error appears in the above-identified patent and that said Letters Patent is hereby corrected as shown below:

On the Title Page

List of Inventors:
• Replace "(72) Inventors: Christopher C. Benevides, Tiverton, MA (US);" with "(72) Inventors: Christopher C. Benevides, Tiverton, RI (US);"

In the Claims

Column 8, Claim 27:
• In Line 63, delete the words "a spray tip" after the words "for transporting the sample fluid from"

Signed and Sealed this
Fourth Day of July, 2017

Joseph Matal
*Performing the Functions and Duties of the*
*Under Secretary of Commerce for Intellectual Property and*
*Director of the United States Patent and Trademark Office*